(12) United States Patent
Salven et al.

(10) Patent No.: US 6,969,045 B2
(45) Date of Patent: Nov. 29, 2005

(54) ROTARY VALVE

(75) Inventors: Owe Salven, Uppsala (SE); Jan Kranse, Uppsala (SE); Patrik Kallback, Uppsala (SE)

(73) Assignee: Amersham Biosciences AB, Uppsala (SE)

( * ) Notice: Subject to any disclaimer, the term of this patent is extended or adjusted under 35 U.S.C. 154(b) by 92 days.

(21) Appl. No.: 10/416,441

(22) PCT Filed: Nov. 22, 2001

(86) PCT No.: PCT/EP01/13589

§ 371 (c)(1),
(2), (4) Date: May 9, 2003

(87) PCT Pub. No.: WO02/42667

PCT Pub. Date: May 30, 2002

(65) Prior Publication Data
US 2004/0021113 A1  Feb. 5, 2004

(30) Foreign Application Priority Data
Nov. 24, 2000  (SE) .................................. 0004341

(51) Int. Cl.[7] .............................................. F16K 5/10
(52) U.S. Cl. .................. 251/208; 251/304; 137/625.46
(58) Field of Search ............................... 251/208, 304; 137/625.46

(56) References Cited

U.S. PATENT DOCUMENTS

| | | |
|---|---|---|
| 3,477,207 A | 11/1969 | Auger |
| 3,837,360 A | 9/1974 | Bubula |
| 3,868,970 A | 3/1975 | Ayers et al. |
| 5,419,208 A * | 5/1995 | Schick .................... 73/863.73 |
| 5,803,117 A | 9/1998 | Olsen et al. |
| 6,012,487 A | 1/2000 | Hauck |

* cited by examiner

*Primary Examiner*—Edward K. Look
*Assistant Examiner*—John K. Fristoe, Jr.
(74) *Attorney, Agent, or Firm*—Royal N. Ronning, Jr.; Yonggang Ji

(57) ABSTRACT

The present invention relates to valves with small dead volumes. A valve in accordance with the present invention has a ferrule (7) which receives a plurality of fluid lines (33) which lead to outlets on an end surface (25) of said ferrule (7) and a movable selector body (15) which has a fluid groove (37, 37A) on a surface (23) which is in contact with the end surface (25) of said ferrule (7). Means are provided for exerting a clamping force on said ferrule (7) in order to simultaneously clamp all the fluid lines (33).

2 Claims, 4 Drawing Sheets

ROTARY VALVE

FIELD OF THE INVENTION

The present invention relates to devices of the type mentioned in the preambles of the independent claims.

PRIOR ART

When performing analysis of liquids using methods such as high pressure liquid chromatography, mass spectrometry and electrophoresis, it is often the case that the specimens of interest are only available in very small volumes or it is desirable to use only very small volumes of specimens e.g. volumes in the order of a hundred nanolitres or less. Often the analytical instrument, for example a high pressure liquid chromatograph (BPLC) has a number of specimen input capillaries that can be selectively connected via a valve to the input of a chromatography column. A rotary valve for this purpose is shown in U.S. Pat. No. 5,419,208. A problem that occurs in practice when applying such small volumes to the analytical instrument is the dead volume of the passageway in the rotatable selector tip of the valve. Typically, such selector tips have dead volumes of the order of 100 nanolitres or more, which means that when small specimen volumes are used, the specimen becomes diluted or contaminated or dispersed. This places a restriction on the number of valves that can be used in an analysis system and gives a limit to just how small a specimen volume can be, and these restrictions make such systems less flexible.

SUMMARY OF THE INVENTION

According to the present invention, at least some of the problems with the prior art are solved by means of a valve device having the features present in the characterising part of claim 1, a ferrule having the features mentioned in the characterising part of claim 1 and a selector body having the features of the characterising part of claim 1. Further improvements are obtained by devices having the features mentioned in the dependent claims.

Further improvements are provided by the features mentioned in the characterising parts of the dependent claims.

BRIEF DESCRIPTION OF THE FIGURES

The following figures show an illustrative, non-limiting example of an embodiment of the present invention in which.

DETAILED DESCRIPTION OF EMBODIMENTS ILLUSTRATING THE INVENTION

Figure 1:
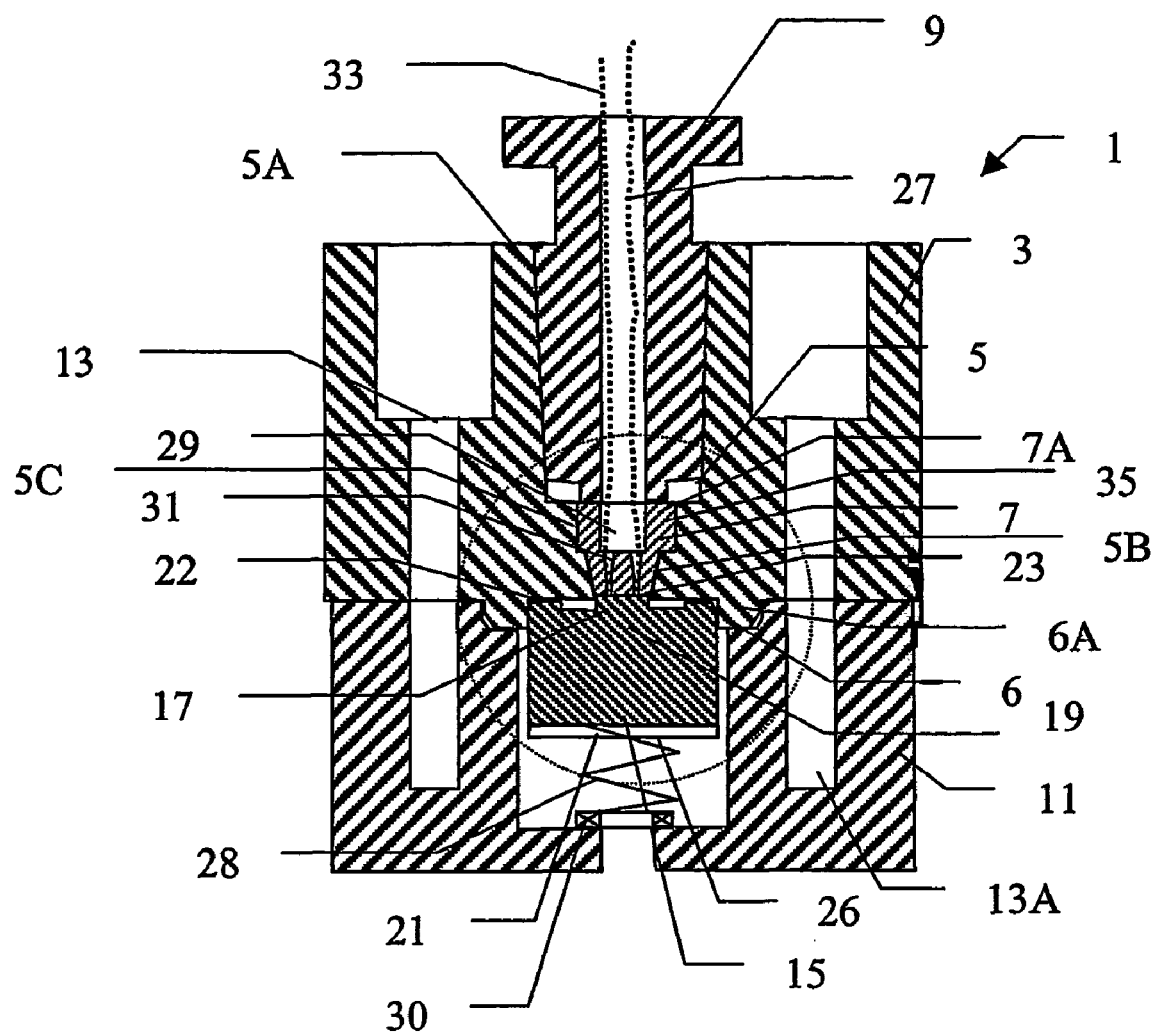
FIG. 1 shows a cross-section of a first embodiment of a valve in accordance with the present invention.
Figure 2:
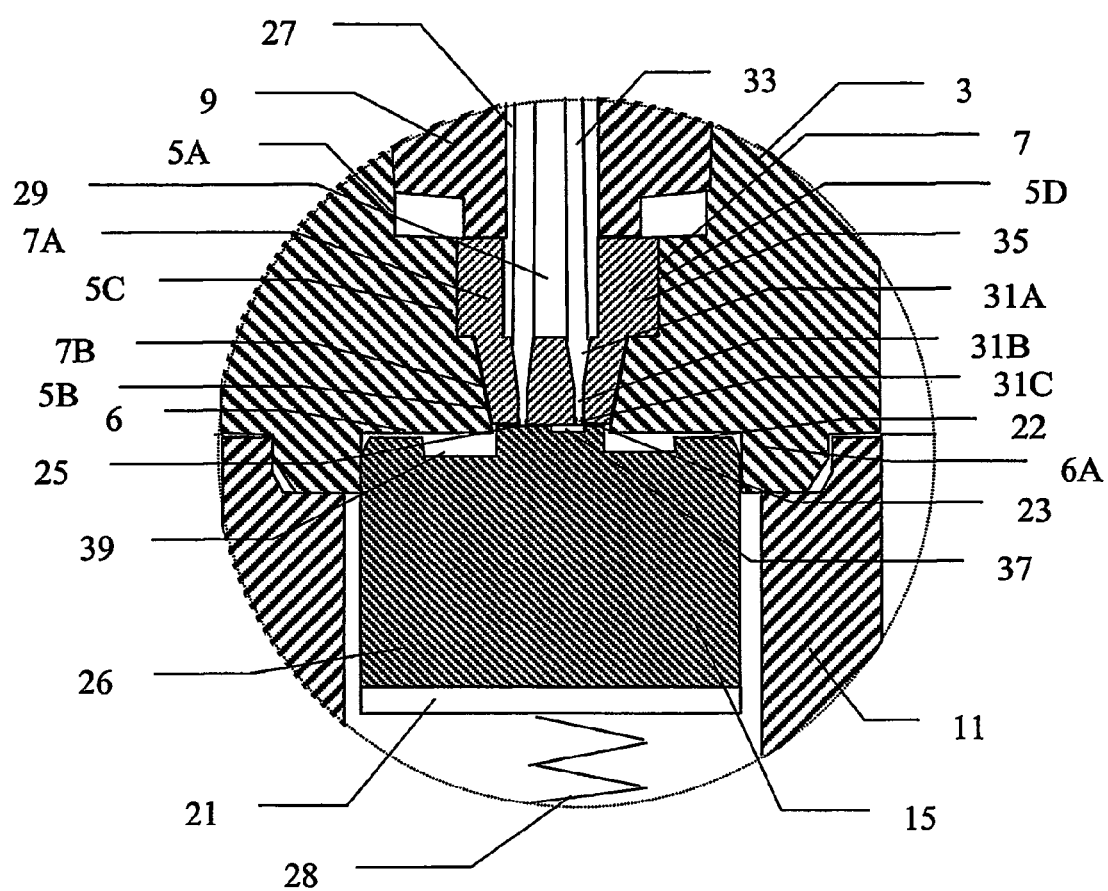
FIG. 2 shows an enlarged view of a portion of FIG. 1.

A rotary valve 1 in accordance with the present invention is shown in section in FIG. 1 and details of the valve are shown enlarged in FIG. 2. Valve 1 has a body 3 with an axial through hole 5. Body 3 is made of any suitable material, such as stainless steel, which is able to withstand the forces exerted during assembly and operation of the valve. Through hole 5 opens out onto a selector body locating surface 6 that has a annular side wall 6A intended to laterally guide a selector body 15 (described in more detail below). The upper end 5A of through hole 5 is preferably cylindrical and the lower end 5B of through hole 5 is conically tapered so that it is narrowest at its bottom. The intermediate part 5C of hole 5 has a non-circular cross-sectional shape so that it can prevent rotation of a ferrule 7, which has a non-circular upper end 7A, e.g. rectangular or oval, intended to co-operation with the intermediate part 5C of through hole 5 to prevent rotation of the ferrule 7, and a conically tapered bottom end 7B. Ferrule 7 is dimensioned so as to be able to fit sufficiently far down in through hole 5 such that it is possible to compress the bottom end 7B against the tapered lower end 5B of through hole 5. Through hole intermediate part 5C is provided with a recess 5D which co-operates with a stub 35 on ferrule 7 to prevent ferrule 7 from rotating once it had been inserted into through hole 5. Ferrule 7 is made of a material that is less rigid than the material used for body 3, for example PEEK (polyetheretherketone). The upper end 5A of through hole 5 has a female screw thread which co-operates with the male screw thread on a ferrule presser 9 that is adapted to fit into through hole 5. Ferrule presser 9 is made of any suitable material, such as stainless steel, which is more rigid than the material used for ferrule 7. Ferrule presser 9 can be screwed down into through hole 5 to force the tapered surface 7B of ferrule 7 against the tapered portion 5B of through hole 5. The ferrule 7 can thereby be compressed between the tapered portion 5B of through hole 5 and ferrule presser 9. As both body 3 and ferrule presser 9 are both more rigid than ferrule 7 then ferrule 7 deforms first under the compression forces.

An end piece 11 is removably attached to the base of body 3 by removable fasteners (not shown) which can be fitted in axial fastener holes 13, 13A in body 3 and end piece 11, respectively. End piece 11 retains and guides into position a selector body, such as rotatable rotor 15, against body 3 and ferrule 5, and is designed to be more rigid than ferrule 7. Rotor 15 is substantially cylindrical with a projecting, substantially concentric boss 17 extending out of the end surface 22 at the end 19 intended to be in contact with ferrule 5. Rotor 15 has means to enable it to be rotated, such as an actuating groove 21 at the end 26 opposite to the boss 17. Boss 17 has a diameter less than the diameter of the bottom of through hole 5 and projects into the through hole 5. Boss 17 has a planar end surface 23 which during use is intended to be in contact with, and seal against, the substantially planar end surface 25 of ferrule 7. The force with which ferrule 7 presses against rotor 15 is controlled by preferably resilient force providing means such as one or more springs 28 which are positioned between the end 26 and the end piece 11 opposite the boss so as to push rotor 15 towards ferrule 7. The resilient force providing means 28 are mounted on bearing means 30 in order to prevent them resisting rotation of the rotor 15. The resilient force providing means 28 are preferably provided with means (not shown) for adjusting the force with which it pushes rotor 15 towards ferrule 7.

Figure 3:
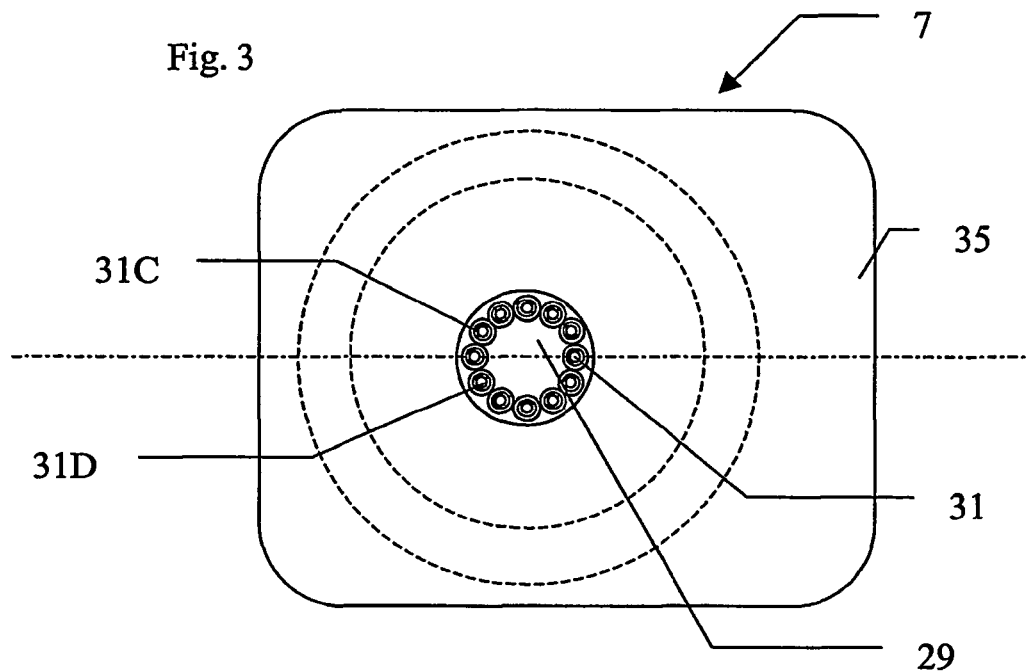
FIG. 3 shows a view from above of a ferrule in accordance with the present invention.
Figure 4:
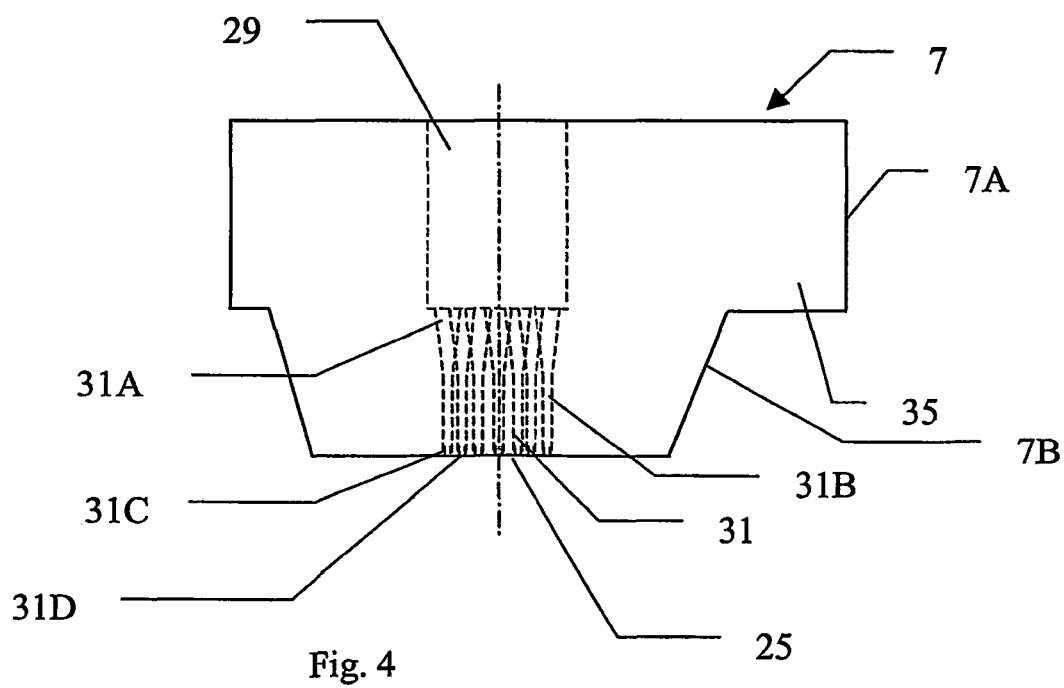
FIG. 4 shows a lateral view of the ferrule from FIG. 3.

Ferrule presser 9 has a hollow core 27, and ferrule 7 has a cylindrical cavity 29 at its upper end. This cavity 29 preferably has the same diameter as, or a greater diameter than, the hollow core 27 of ferrule presser 9 and is substantially concentric with it. This makes it easier to insert capillaries into the ferrule 7, as this ensures that that is no lip between the ferrule 7 and ferrule presser 9 that a capillary can catch on. As can be seen from FIGS. 3 and 4, cavity 29 extends approximately as far as the intersection between the cylindrical portion 7A and tapered portion 7B of ferrule 7. The lower end of cavity 29 contains a plurality of capillary receiving through holes 31 that extend from the base of cavity 29 to the bottom surface of ferrule 7. It is preferable that said through holes are equidistantly spaced as this leads to the clamping forces (described below)on the capillaries 33 being substantially the same for all the capillaries. The upper ends 31A of through holes 31 are tapered so that they become narrower towards the bottom and at approximately half way along their depth they become cylindrical, so that the lower ends 31B of through hole 31 are cylindrical. The diameter of the lower ends 31B of capillary through holes 31 when uncompressed is substantially the same as, or greater than, the diameter of the fluid tubing such as capillaries 33 (shown by dotted lines in FIG. 1) with which the valve is intended to be used, e.g. 0.36 mm if silica capillaries are used or 0.18 mm if micro-silica capillaries are used, except at the very bottom, where a ledge 31C is provided to form an end stop 31C. The height of the ledge could be 0.2 mm or less. This prevents the capillaries 33 from being inserted too far into through holes 31 and projecting out of the bottom surface 25 of ferrule 7. End stop 31C has a orifice 31D to allow fluid to pass through the bottom of the ferrule 7. In order to make the valve as small as possible, the distance between centres of the capillary through holes 31 can be small, for example of the order of 0.5 mm if silica capillaries with an outside diameter of 0.36 mm are used and 0.25 mm if micro-silica capillaries (outside diameter 0.18 mm) are used. Despite the small distance between centres, by appropriate choices of material for the ferrule 7 and connector body 3, and by using shapes for these components so that the stresses in the ferrule as it clamps the capillaries are distributed so that it is not damaged while at the same time it grips the capillaries securely, a number of capillaries can be connected to the valve in a very small area Thus four 0.18 mm diameter capillaries could be arranged in square in a ferrule with distance between centres of adjacent capillaries of 0.25 mm. The distance between centres of diagonally opposed capillaries would then be 0.35 mm.

The very small area also has another great advantage, namely, it decreases the contact force between ferrule 7 and rotor 15. The very small contact surface also decreases the torque needed to turn rotor 15. This means that only a very small actuator, such as a miniature electrical motor, is necessary to turn the valve and this makes the size of the whole valve very small.

The tapered upper ends 31A of capillary through holes 31 act as funnels and make it easier to thread the capillaries 33 in the capillary through holes 31. Ferrule 7 is preferably provided with means for preventing it from rotating once it has been placed in body 3, in order to prevent capillaries from becoming twisted and to ensure that the correct capillaries are connected when the valve is actuated. This can be achieved in many different ways, for example by making it asymmetric, e.g. by providing a projecting stub 35, and by providing body 3 with a complementary recess (e.g. intermediate part 5C), so that ferrule 7 can be held fixed against rotation with respect to body 3.

Figure 5:
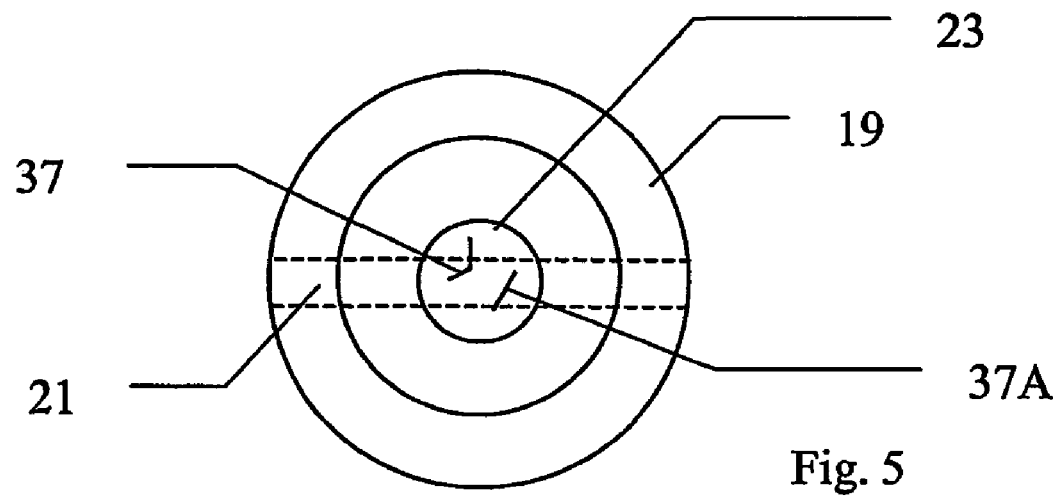
FIG. 5 shows a view from above of a rotor in accordance with the present invention.
Figure 6:
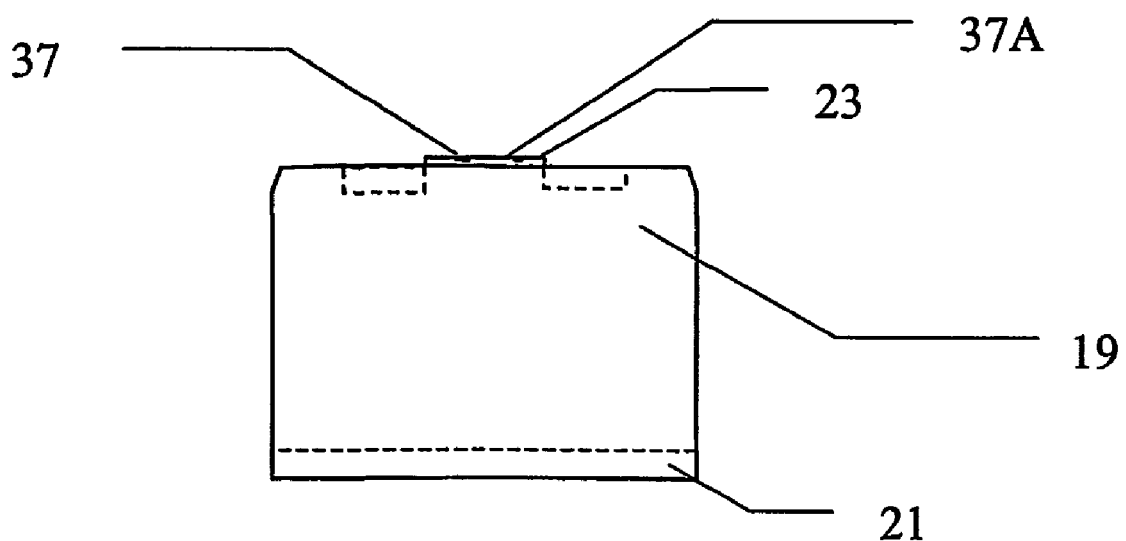
FIG. 6 shows a cross-section through line VI—VI in FIG. 5.

As shown more clearly in FIGS. 5 and 6, the planar end surface 23 of boss 17 of rotor 15 is provided with one or more fluid grooves 37, 37A which, in order to keep the dead volume as small as possible, can be 0.2 mm or less in width and depth and which can be positioned as desired in order to enable two or more capillaries to be connected to each other via a fluid groove 37, 37A. Thus in the example above of four 0.18 mm capillaries, the maximum length of a groove needed to connect the centres of two diagonally opposed capillaries would be 0.35 mm. If the groove had a-square cross-section that was 0.15 mm wide and 0.15 mm deep then the volume of the groove would be 0.15 mm×0.15 mm×0.35 mm=7.875×10$^{-12}$ m$^3$ (nanolitres). Preferably, boss 17 is surrounded by an annular groove 39, which extends a short distance down into rotor 15. This is to ensure that when rotor 15 is fitted against ferrule 7 the end face of rotor 15 does not come into contact with the end face of body 3. This means that in the axial direction, at the boss end of the rotor 15, the only part of rotor 15 facing towards the ferrule that is in contact with another surface is the end surface of 23 of boss 17 and this ensures that the resistance to rotation of rotor 15 is low.

A valve in accordance with the present invention can be assembled in the following way: the operator threads the required number of capillaries 33 through the hollow core 27 of ferrule presser 9. A first capillary 33 is then introduced into cavity 29 of ferrule 7, fed into the tapered upper end 31A of a first through hole 31 and pushed approximately all the way into the lower end 31B of the through hole 31 until it reaches the end stop 31C near the bottom of the through hole 31. This is repeated for a second capillary and a second through hole, until all the capillaries 33 have been mounted in their respective through holes 31. The ferrule 7 is then positioned in the through hole 5 with its stub 35 located in the corresponding recess 5D in through hole 5, with its tapered bottom end 7B located in the tapered lower end 5B of through hole 5. The ferrule presser 9 is introduced into the through hole 5 in body 3. The thread on the outside of ferrule presser 9 is brought into contact with the thread on the inside of through hole 5 and ferrule presser 9 is rotated with respect to body 3 so that it descends through hole 5 until ferrule 7 is lightly pressed into the tapered bottom end 5B of through hole 5. Rotor 15 is then placed with its boss 17 projecting into the bottom of through hole 5 and with its end surface 22 in contact with the surface 6 of body 3. Rotor 15 is aligned with through hole 5 with the help of side wall 6A. End piece 11 in then mounted against the bottom of body 3 in order to hold rotor 15 in place. Ferrule presser 9 is then screwed further down into through hole 5 so that ferrule 7 is compressed between ferrule presser 9 and the tapered end 5B of through hole 5, and so that the end surface 25 of ferrule 7 comes into contact with rotor boss end surface 23 and pushes rotor 15 in the direction out of through hole 5 against the spring force of springs 28 so that rotor surface 22 is no longer in contact with surface 6 of body 3. This reduces the resistance to rotation of rotor 15. As the ferrule 7 is less rigid that the body 3 in the region around tapered end 5B of through hole 5, the tapered part of the lower end 7B of ferrule 5 deforms. One of the few directions in which the material can deform is towards the inside of the ferrule through holes 31. This causes a radial force towards the centre of each fluid line receiving through hole 31. This results in a clamping force on the capillaries 33 introduced into the through holes 31. This clamping force can be increased by screwing ferrule presser 9 deeper into through hole 5 and can easily be enough to form a fluid tight seal which can resist over 1000 bar—a pressure which has been difficult to achieve in prior art valves for use in high pressure liquid chromatography, mass spectrometry and electrophoresis and the like. If the fluid line receiving holes are arranged symmetrically, then the clamping force on each capillary is substantially equal. As the capillaries are all held in one ferrule then the distance between each capillary can be minimised. This means that the distance between the open ends of-the fluid line receiving through holes can also be minimised which allows the and therefore the length of the fluid grooves 37, 37A to be mimised.

Connections between capillaries can be made by rotating rotor 15, for example manually by means of a screwdriver or knob acting on the groove, or automatically by means of the suitably shaped shaft of an electric motor or a gearbox, inserted into actuating groove 21, until fluid groove 37 or 37A unites the desired capillaries 33.

It is conceivable to provide a valve in accordance with the present invention in which the ferrule presser is provided with a plurality of axial guide holes for capillaries instead of a hollow centre. Each guide hole would have an outlet at the bottom of the ferrule presser and the outlet would be arranged to align with capillary through holes in the ferrule. The ferrule and ferrule presser could be provide with co-operating alignment means such as a projection on one component of these components which fits into a recess on the other component. As this would make it undesirable to have a ferrule presser which is screwed into the valve body (as this would twist the capillaries and be difficult to align with the holes in the ferrule) other means such as axially movable clamps could be provided in order to press the ferrule presser against the ferrule. Alternatively the ferrule pressure could be made of two or more parts, one of which acts as a capillary guiding means and does not rotate, while another rotatable part can be screwed into the valve body to compress the ferrule and, preferably, retain the capillary guiding means.

While the embodiment of the present invention illustrated in the figures depicts a valve in which the ferrule and selector body have flat co-operating surfaces, it is of course possible to use other surface shapes which can seal against each other while still permitting relative movement between each other, such as semi-spherical, or conical. For example, a ferrule can have a concave surface and a selector body a matching convex surface, or vice versa.

Furthermore, it is also conceivable to provide selector bodies which do not rotate but which move in other ways. For example, the fluid grooves could be made in a surface of an elongated selector body, such as a bar or rod. This elongated selector body could be positioned under the ferrule with the surface having the fluid grooves facing towards, and in sealing contact with the end surface of the ferrule. The elongated selector body could be movable in the transverse direction so that different connections between capillaries could be achieved by sliding the elongated selector body until the appropriate fluid groove was positioned under the capillaries of interest.

It is also conceivable to provide ferrules having different shapes, for example having a truncated pyramid shaped bottom end, intended to fit in a through hole end having a complementary shape which can exert a radial force on the ferrule. Another conceivable design for a ferrule could have a cylindrical bottom end. This could be compressed by being forced down into a tapering through hole in order to seal around capillaries inserted in it.

The above mentioned example of conceivable embodiments are intended to illustrate the present invention and are not intended to limit the scope of protection claimed by the following claims.

What is claimed is:

1. A valve (1) for selectively coupling together two or more fluid lines (33), comprising a ferrule (7) having a plurality of fluid line receiving through holes (31), each said through hole (31) being capable of receiving one of said fluid lines (33) and further having an orifice (31D) that opens onto a surface (25) of said ferrule (7), wherein said valve further contains a movable selector body (15) comprising at least one fluid groove (37, 37A) for selectively connecting two or more of said orifices (31D), wherein said at least one fluid groove (37, 37A) is provided on a surface (23) of said selector body which is in contact with, and seals against, said surface (25) of said ferrule (7), wherein said selector body (15) further includes means (5B) for exerting a force on said ferrule (7) in order to simultaneously exert a fluid line clamping force on all said fluid line receiving through holes (31) and further, wherein said ferrule (7) is held in a valve body (3) which is more rigid than said ferrule (7).

2. A valve (1) for selectively coupling together two or more fluid lines (33), comprising a ferrule (7) having a plurality of fluid line receiving through holes (31), each said through hole (31) being capable of receiving one of said fluid lines (33) and further having an orifice (31D) that opens onto a surface (25) of said ferrule (7), wherein said valve further contains a movable selector body (15) comprising at least one fluid groove (37, 37A) for selectively connecting two or more of said orifices (31D), wherein said at least one fluid groove (37, 37A) is provided on a surface (23) of said selector body which is in contact with, and seals against, said surface (25) of said ferrule (7), wherein said selector body (15) further includes means (5B) for exerting a force on said ferrule (7) in order to simultaneously exert a fluid line clamping force on all said fluid line receiving through holes (31) and further, wherein the upper ends (31A) of said through holes (31) are tapered so that they become narrower towards the bottom.

* * * * *